United States Patent
Yang et al.

(10) Patent No.: US 8,795,739 B2
(45) Date of Patent: Aug. 5, 2014

(54) IRON FORTIFIED FOOD PRODUCT AND ADDITIVE

(75) Inventors: Shieh-Yueh Yang, Taipei (TW); Che-Chuan Yang, Taipei (TW)

(73) Assignee: Magqu Co. Ltd., New Taipei (TW)

( * ) Notice: Subject to any disclaimer, the term of this patent is extended or adjusted under 35 U.S.C. 154(b) by 119 days.

(21) Appl. No.: 13/530,547

(22) Filed: Jun. 22, 2012

(65) Prior Publication Data

US 2013/0344113 A1    Dec. 26, 2013

(51) Int. Cl.
*A01N 59/16*    (2006.01)
(52) U.S. Cl.
USPC .................................................. 424/646
(58) Field of Classification Search
None
See application file for complete search history.

(56) References Cited

U.S. PATENT DOCUMENTS

2011/0081451 A1*    4/2011    Siegel et al. .............. 426/61

* cited by examiner

*Primary Examiner* — Carlos Azpuru
*Assistant Examiner* — Casey Hagopian
(74) *Attorney, Agent, or Firm* — WPAT, P.C.; Anthony King

(57) ABSTRACT

The present invention relates to a food product which has been fortified in iron content, comprising a $Fe_3O_4$ sphere. The present invention also relates to an iron-containing additive for use in the above food product, in the form of a $Fe_3O_4$ sphere. The present invention further relates to a method for preparing the above food product, comprising the steps of adding or mixing the iron-containing additive in solid or dispersed form with the food product, wherein the iron-containing additive is in the form of a $Fe_3O_4$ sphere.

16 Claims, 3 Drawing Sheets

IRON FORTIFIED FOOD PRODUCT AND ADDITIVE

FIELD OF THE INVENTION

The present invention generally relates to the field of fortified food products. More in particular, it relates to the fortification of a food product with iron. The invention also relates to an additive for the fortification and supplementation of food products and other products with iron and to a method of preparing the same.

BACKGROUND OF THE INVENTION

Iron is an essential trace element in animal and human nutrition. It is a component of heme in hemoglobin and of myoglobin, cytochromes and several enzymes. The main role of iron is its participation in the transport, storage and utilization of oxygen.

Iron deficiency was and remains a common nutritional problem not only in the developing world but also in the industrialized countries. Inadequate intake of dietary iron causes the high incidence of anemia which nutritional surveys have identified among children, adolescents and women. Since the human body does not produce minerals, it is totally dependent on an external supply of iron, either nutritional or supplementary. The importance of adequate iron intake is recognized during the whole life of the human being.

Iron(II,III) oxide is the chemical compound with formula $Fe_3O_4$. It is one of a number of iron oxides, the others being iron(II) oxide (FeO), which is rare, and iron(III) oxide ($Fe_2O_3$) also known as hematite. It occurs in nature as the mineral magnetite. It contains both $Fe^{2+}$ and $Fe^{3+}$ ions and is sometimes formulated as $FeO.Fe_2O_3$. Nano particles of $Fe_3O_4$ are used as contrast agents in MRI scanning. Further, $Fe_3O_4$ can be cost effectively produced. Production of $Fe_3O_4$ nano-particles can be performed chemically by taking for example mixtures of FeII and FeIII salts and mixing them with alkali to precipitate colloidal Fe3O4. The reaction conditions are critical to the process and determine the particle size.

An important feature for the iron containing compounds used as additive in a food product is the bioavailability of the iron i.e. how efficiently the iron is absorbed by the body. However, some iron containing compounds with high bioavailability are highly irritative to stomach and not being able to be used on food products, such as $FeSO_4$. Iron powder and iron salt are disclosed in previous study as potential food additive, but the cost of producing them is relatively higher. Therefore, there is a need to search an iron containing compound with low production cost but possessing characteristics of both high bioavailability and low irritation to body.

SUMMARY OF THE INVENTION

The present invention relates to a food product fortified in iron content, comprising a $Fe_3O_4$ sphere. The present invention also relates to an iron-containing additive for use in the above food product, in the form of a $Fe_3O_4$ sphere. The present invention further relates to a method for preparing the above food product, comprising the steps of adding or mixing the iron-containing additive in solid or dispersed form with the food product, wherein the iron-containing additive is in the form of a $Fe_3O_4$ sphere.

DETAILED DESCRIPTION OF THE INVENTION

The present invention is to investigate the bioavailability of $Fe_3O_4$ spheres in the body.

The present invention finds that the $Fe_3O_4$ spheres has a relatively high bioavailability and is potential for being used as an additive for food products.

The terms used in the description herein will have their ordinary and common meaning as understood by those skilled in the art, unless specifically defined otherwise.

The term "food product" used in the specification refers to all products which can be orally used, such as food, drinks, medicine, nutrient supplements and animal feed.

Figure 1:
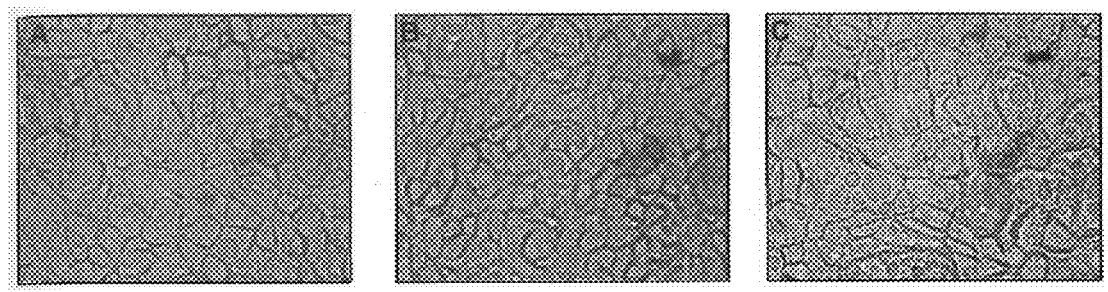
FIG. 1 shows the morphology of the Caco-2 cells after 24 hours treatment. (A) Positive control: 50 µM $FeSO_4$; (B) Negative control: Phosphate buffered saline; (C) High dose group: Treated with 100 µM $Fe_3O_4$.
Figure 2:
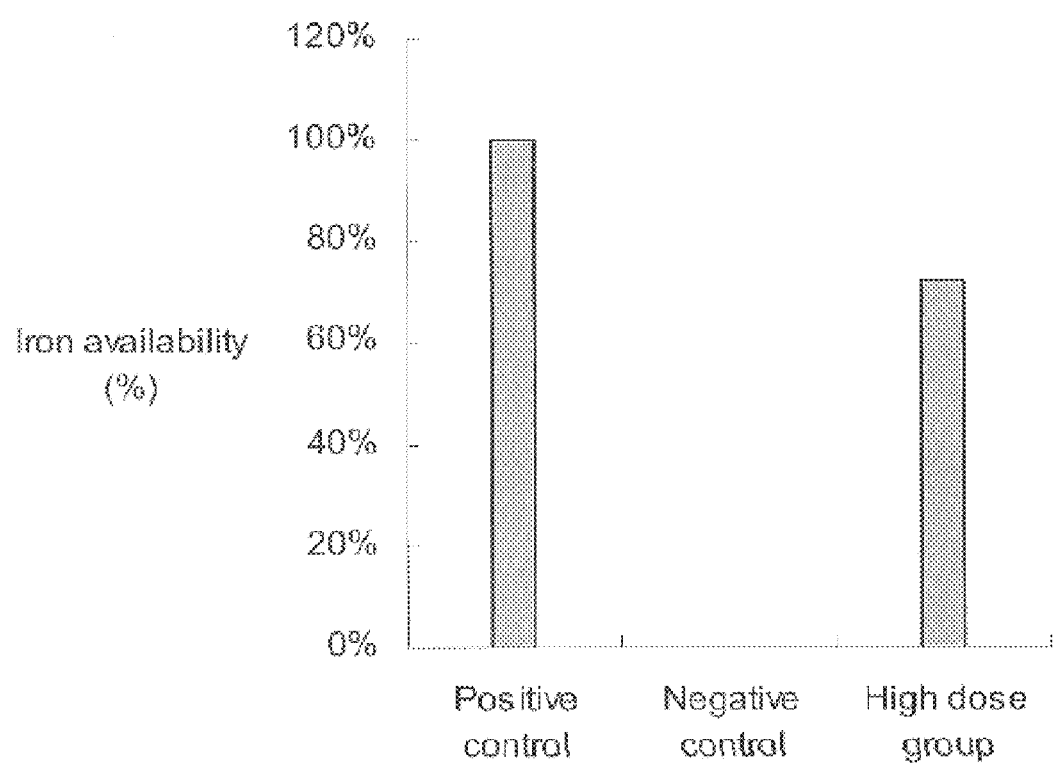
FIG. 2 shows the iron availability of the test group. Positive control: 50 µM $FeSO_4$; Negative control: Phosphate buffered saline; High dose group: Treated with 100 µM $Fe_3O_4$.
Figure 3:
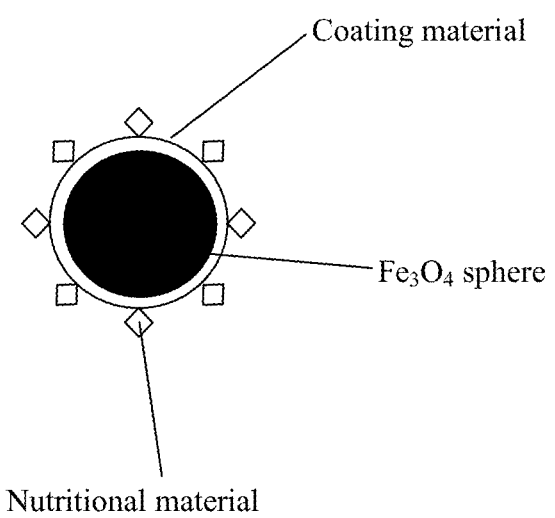
FIG. 3 is a schematic diagram showing the $Fe_3O_4$ sphere which is coated by a coating material bound to a nutritional material.

Thus, the present invention provides a food product fortified in iron content, comprising a $Fe_3O_4$ sphere. In a preferred embodiment, the diameter of the $Fe_3O_4$ sphere is less than 5000 nanometer. Preferably, the diameter of the $Fe_3O_4$ sphere is between 30-3000 nanometer. In a more preferred embodiment, the $Fe_3O_4$ sphere is coated by a coating material selected from surfactants. Preferably, the surfactants are selected from the group consisting of emulsifiers, polysaccharides and oils. The emulsifiers include, but not limited to, fatty acid esters, collagen and polysorbate. The polysaccharides include, but not limited to, alginate, dextran, dextrin and amylopectin. The oils include, but not limited to, palm oil, coconut oil, glycerin and liposome. In a further preferred embodiment, the coating material is bound to a nutritional material which is, for example, ascorbic acid, folic acid or herb extracts, as FIG. 3 shows. It is noted that the coating material and the nutritional material are both optional for the $Fe_3O_4$ sphere. In a preferred embodiment, the food product is selected from the group consisting of food, drinks, nutrient supplements, nutrients, medicine and animal feed.

The present invention also provides an iron-containing additive for use in the above food product, in the form of a $Fe_3O_4$ sphere. In a preferred embodiment, the diameter of the $Fe_3O_4$ sphere is less than 5000 nanometer. Preferably, the diameter of the $Fe_3O_4$ sphere is between 30-3000 nanometer. In a more preferred embodiment, the $Fe_3O_4$ sphere is coated by a coating material selected from surfactants. Preferably, the surfactants are selected from the group consisting of emulsifiers, polysaccharides and oils. The emulsifiers include, but not limited to, fatty acid esters, collagen and polysorbate. The polysaccharides include, but not limited to, alginate, dextran, dextrin and amylopectin. The oils include, but not limited to, palm oil, coconut oil, glycerin and liposome. In a further preferred embodiment, the coating material is bound to a nutritional material which is, for example, ascorbic acid, folic acid or herb extracts, as FIG. 3 shows. It is noted that the coating material and the nutritional material are both optional for the $Fe_3O_4$ sphere.

The present invention further provides a method for preparing the above food product, comprising the steps of adding or mixing the iron-containing additive in solid or dispersed form with the food product, wherein the iron-containing additive is in the form of a $Fe_3O_4$ sphere. In a preferred embodiment, the diameter of the $Fe_3O_4$ sphere is less than 5000 nanometer. Preferably, the diameter of the $Fe_3O_4$ sphere is between 30-3000 nanometer. In a more preferred embodiment, the $Fe_3O_4$ sphere is coated by a coating material selected from surfactants. Preferably, the surfactants are selected from the group consisting of emulsifiers, polysaccharides and oils. The emulsifiers include, but not limited to, fatty acid esters, collagen and polysorbate. The polysaccharides include, but not limited to, alginate, dextran, dextrin and amylopectin. The oils include, but not limited to, palm oil, coconut oil, glycerin and liposome. In a further preferred embodiment, the coating material is bound to a nutritional material which is, for example, ascorbic acid, folic acid or herb extracts, as FIG. 3 shows. It is noted that the coating material and the nutritional material are both optional for the $Fe_3O_4$ sphere.

EXAMPLES

The examples below are non-limiting and are merely representative of various aspects and features of the present invention.

Example 1

The assay followed the guidance of Department of Health, Executive Yuan, R.O.C. (TAIWAN) and was conducted to analyze the cytotoxicity and the iron bioavailability of $Fe_3O_4$ microspheres in the in vitro digestion/Caco-2 cell culture system. The iron bioavailability from the test article could be evaluated by an in vitro system including enzymatic digestion, iron uptake and ferritin determination via an Enzyme-linked immunosorbent assay (ELISA).

Method:
Cell Culture:
  Cell line: Human colon adenocarcinoma, clone of Caco-2. BCRC 80182.
  Culture medium: Minimum Essential Medium (MEM) without any additional iron, iron conc.<8 μg/L.
  Culture condition: $37\pm1°$ C. with 5% $CO_2$ incubator.
  EBSS/MES buffer: Earle's balanced salt solution (EBSS)˙10 mM MES (2-[4-morpholino]-ethanesulfonic acid) buffer, pH 6.0.
  MEM enrichment medium: hydrocortisone (4 mg/L)˙10 mM PIPES (piperazine-N,N'-bis-[2-ethanesulfonic acid])˙1% antibiotic-antimycotic solution˙insulin (5 mg/L)˙sodium selenite (5 μg/L)˙triiodothyronine (34 Mg//L) and epidermal growth factor (2 μg//L).
  Iron removal solution: 1 mM bathophenanthroline disulfonic acid (BPDS) and 5 mM sodium hydrosulfite were dissolved in the rinse solution.
  Rinse solution: 140 mM NaCl˙5 mM KCl˙10 mM PIPES, pH 7.0.
Grouping:

TABLE 1

The groups in our test

| Group | Positive Control | Negative Control | High Dose | Middle Dose | Low Dose |
|---|---|---|---|---|---|
| Test article concentration | $FeSO_4$ 50 μM | PBS 0 | $Fe_3O_4$ 100 μM | $Fe_3O_4$ 50 μM | $Fe_3O_4$ 10 μM |

Positive Control: The iron control solution. The $FeSO_4$ was dissolved in the fresh prepared EBSS/MES. The final concentration was 50 μM.
Negative Control: Phosphate buffered saline without any iron.
Test group: The digested solution of $Fe_3O_4$ microsphere. There were three $Fe_3O_4$ concentration used in this study, included high (100 μM), middle (50 μM) and low (10 μM) dose groups.

Test Article:
The test article were two sizes of $Fe_3O_4$ microspheres with an average diameter of 800 nanometer (nm) and 3000 nm, respectively. Both microspheres were placed in a buffer with a pH value ranges from 5-7. Preferably, the buffer was water or Phosphate Buffered Saline (PBS). In this experiment, the buffer was Phosphate Buffered Saline.

Procedure:
The digestion of the test article: 0.5 mL of test article was dissolved in 1 mL of 1 N HCl solution, and incubated at $37\pm1°$ C. for 16 hours. The final iron concentration was 100 μM. Phosphate buffered saline was used as the negative control and treated in the same condition without the test article.

Iron bioavailability test:
  i. When the Caco-2 cells which were cultured in the 67 well plate for 12-14 days were reached to 90-100% confluency, the culture medium was removed and washed the Caco-2 cells twice with MEM medium. 2 mL of MEM enrichment medium contained digested solution of MB-0800 and MB-3000 or control solution were placed into marked wells
  ii. Incubated at $37\pm1°$ C. with 5% $CO_2$ for 24 hours. When the cells were incubated for 24 hours, the medium was removed and replaced with 2 mL of rinse solution. Then the rinse solution was aspirated.
  iii. 2 mL of the freshly prepared iron removal solution was incubated with the Caco-2 cells for 10 min. Aspirated the iron removal solution and then added 2 ml of rinse solution to wash the cells. Aspirated the rinse solution.
  iv. The cell lysates in each well were collected with 2 mL of deionized water and homogenized in a sonicator for 15 min.
  v. Using less cytotoxicity group to analyze total protein and ferritin analysis.

Total protein analysis:
  i. Total protein determination was performed by the Bradford method. Briefly, 200 μL of the Bradford reagent was mixed with 100 μL of the 10× sample or standard, and incubated for 1~5 min. Measured the absorbance at 595 nm with an ELISA reader.
  ii. Used the standard curve regression to calculate the concentration in the unknown samples.

Ferritin analysis:
  i. Determined by, the human ferritin enzyme immunoassay test kit.
  ii. Dispensed 20 μL of the standard, specimens, and controls into the appropriate wells. 100 μL of the Enzyme Conjugate Reagent was added into each well and thoroughly mixing for 30 seconds. Then the mixtures were incubated at room temperature for 60 minutes.
  iii. Removed the incubation mixture and rinsed the microplate for 5 times with the deionized water. Then the residual water should be removed thoroughly.
  iv. Dispensed 100 μL of the TMB solution into each well and then incubated at room temperature in the dark for 20 minutes.
  v. Stopped the reaction by adding 100 μL of the Stop Solution to each well and then measured the absorbance at 450 nm with the ELISA reader.

Evaluation criterion:
If the iron availability represented that the iron of the test group was more than negative group, it represented that the iron of test article can be absorbed by the cells.

Results:

The $Fe_3O_4$ microspheres could be digested completely with 1 N HCl. In the result, the Caco-2 cell didn't show any cytotoxicity after the digested $Fe_3O_4$ microspheres treatment. The amounts of the total protein of the positive control, negative control and high dose group were 238.8±13.3, 264.7±17.4 and 320.2±11.3 μg/mL, respectively. The tested ferritin values of the positive control, negative control and high dose group were 61.1±1.6, 0.0±0.0 and 59.0±3.2 ng/mL, respectively. The final ferritin values were calibrated by total protein and the calibrated values of the positive control, negative control and high dose group were 255.9±15.4, 0.0±0.0 and 184.1±9.1 ng/mg protein, respectively.

TABLE 2

The results of the Iron availability test

| Group | Total protein (μg/mL) | Tested Ferritin (ng/mL) | Calibrated Ferritin (ng/mg protein) | Iron availability (%) |
|---|---|---|---|---|
| Positive control[a] | 238.8 ± 13.3 | 61.1 ± 1.6 | 255.9 ± 15.4 | 100% |
| Negative control[b] | 264.7 ± 17.4 | 0.0 ± 0.0 | 0.0 ± 0.0 | 0% |
| High dose group[c] | 320.2 ± 11.3 | 59.0 ± 3.2 | 184.1 ± 9.1 | 72.0% |

[a]Treated with 50 μM $FeSO_4$
[b]Treated with Phosphate buffered saline
[c]Treated with 100 μM $Fe_3O_4$ One skilled in the art readily appreciates that the present invention is well adapted to carry out the objects and obtain the ends and advantages mentioned, as well as those inherent therein. The food products, food additives and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A food product fortified in iron content, comprising a $Fe_3O_4$ sphere, wherein the $Fe_3O_4$ sphere is coated by a coating material bound to a nutritional material.

2. The food product of claim 1, wherein the diameter of the $Fe_3O_4$ sphere is less than 5000 nanometer.

3. The food product of claim 2, wherein the diameter of the $Fe_3O_4$ sphere is between 30-3000 nanometer.

4. The food product of claim 1, wherein the coating material is selected from surfactants.

5. The food product of claim 4, wherein the surfactants are selected from the group consisting of emulsifiers, polysaccharides and oils.

6. The food product of claim 5, wherein the emulsifiers include fatty acid esters, collagen and polysorbate.

7. The food product of claim 5, wherein the polysaccharides include alginate, dextran, dextrin and amylopectin.

8. The food product of claim 5, wherein the oils include palm oil, coconut oil, glycerin and liposome.

9. The food product of claim 1, wherein the nutritional material is selected from the group consisting of ascorbic acid, folic acid and herb extracts.

10. The food product of claim 1, wherein the food product is selected from the group consisting of food, drinks, nutrient supplements, nutrients, medicine and animal feed.

11. An iron-containing additive for use in the food product of claim 1, in the form of a $Fe_3O_4$ sphere, wherein the $Fe_3O_4$ sphere is coated by a coating material bound to a nutritional material.

12. The iron-containing additive of claim 11, wherein the diameter of the $Fe_3O_4$ sphere is less than 5000 nanometer.

13. The iron-containing additive of claim 11, wherein the coating material is selected from surfactants.

14. A method for preparing the food product of claim 1, comprising the steps of adding or mixing the iron-containing additive in solid or dispersed form with the food product, wherein the iron-containing additive is in the form of a $Fe_3O_4$ sphere, wherein the $Fe_3O_4$ sphere is coated by a coating material bound to a nutritional material.

15. The method of claim 14, wherein the diameter of the $Fe_3O_4$ sphere is less than 5000 nanometer.

16. The method of claim 14, wherein the coating material is selected from surfactants.

* * * * *